US00PP24966P2

(12) United States Plant Patent
Konst

(10) Patent No.: US PP24,966 P2
(45) Date of Patent: Oct. 14, 2014

(54) ***ALSTROEMERIA* PLANT NAMED 'KONCASMILE'**

(50) Latin Name: *Alstroemeria hybrida*
Varietal Denomination: Koncasmile

(71) Applicant: Johannes Wilhelmus Maria Konst, Nieuwveen (NL)

(72) Inventor: Johannes Wilhelmus Maria Konst, Nieuwveen (NL)

(73) Assignee: Könst Breeding B.V., Nieuwveen (NL)

( * ) Notice: Subject to any disclaimer, the term of this patent is extended or adjusted under 35 U.S.C. 154(b) by 73 days.

(21) Appl. No.: 13/694,495

(22) Filed: Dec. 6, 2012

(51) Int. Cl.
*A01H 5/00* (2006.01)

(52) U.S. Cl.
USPC ..... Plt./309

(58) Field of Classification Search
USPC ..... Plt./309
See application file for complete search history.

*Primary Examiner* — Annette Para
(74) *Attorney, Agent, or Firm* — C. A. Whealy

(57) ABSTRACT

A new and distinct cultivar of *Alstroemeria* plant named 'Koncasmile', characterized by its compact and mounding plant habit; sturdy and strong plants; vigorous growth habit; freely branching habit; numerous large white, yellow and pink-colored flowers; and good garden performance.

2 Drawing Sheets

Botanical designation: *Alstroemeria hybrida.*
Cultivar denomination: 'KONCASMILE'.

BACKGROUND OF THE INVENTION

The present invention relates to a new and distinct cultivar of *Alstroemeria* plant, botanically known as *Alstroemeria hybrida*, typically grown as a potted garden *Alstroemeria*, and hereinafter referred to by the name 'Koncasmile'.

The new *Alstroemeria* plant is a product of a planned breeding program conducted by the Inventor in Nieuwveen, The Netherlands. The objective of the breeding program is to create new compact potted garden *Alstroemeria* plants that flower early and freely with attractive leaf and flower coloration.

The new *Alstroemeria* plant originated from a cross-pollination made by the Inventor in Nieuwveen, The Netherlands in October, 2008 of a proprietary *Alstroemeria hybrida* selection identified as code number 11-11-0-7, not patented, as the female, or seed, parent with a proprietary *Alstroemeria hybrida* selection identified as code number 12-lele, not patented, as the male, or pollen, parent. The new *Alstroemeria* plant was discovered and selected by the Inventor as a single flowering plant from within the progeny of the stated cross-pollination in a controlled greenhouse environment in Nieuwveen, The Netherlands in November, 2010.

Asexual reproduction of the new *Alstroemeria* plant by in vitro rhizogenesis in a controlled greenhouse environment in Nieuwveen, The Netherlands since November, 2010 has shown that the unique features of this new *Alstroemeria* plant are stable and reproduced true to type in successive generations.

SUMMARY OF THE INVENTION

Plants of the new *Alstroemeria* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Koncasmile'. These characteristics in combination distinguish 'Koncasmile' as a new and distinct *Alstroemeria* plant:

1. Compact and mounding plant habit.
2. Sturdy and strong plants.
3. Vigorous growth habit.
4. Freely branching habit.
5. Numerous large white, yellow and pink-colored flowers.
6. Good garden performance.

Plants of the new *Alstroemeria* can be compared to plants of the female parent selection. Plants of the new *Alstroemeria* differ primarily from plants of the female parent selection in the following characteristics:

1. Plants of the new *Alstroemeria* are more compact than plants of the female parent selection.
2. Plants of the new *Alstroemeria* and the female parent selection differ in flower color as plants of the female parent selection have white-colored flowers.

Plants of the new *Alstroemeria* can be compared to plants of the male parent selection. Plants of the new *Alstroemeria* differ primarily from plants of the male parent selection in flower color as plants of the male parent selection have yellow and yellow orange-colored flowers.

Plants of the new *Alstroemeria* can be compared to plants of the *Alstroemeria hybrida* 'Konpride', disclosed in U.S. Plant Pat. No. 20,050. In side-by-side comparisons conducted in Nieuwveen, The Netherlands, plants of the new *Alstroemeria* differed from plants of 'Konpride' in the following characteristics:

1. Plants of the new *Alstroemeria* were shorter and broader than plants of 'Konpride'.
2. Plants of the new *Alstroemeria* had larger flowers than plants of 'Konpride'.

3. Plants of the new *Alstroemeria* and 'Konpride' differed in flower color as plants of 'Konpride' had bright pink-colored flowers.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet comprises a side perspective view of a typical flowering plant of 'Koncasmile' grown in container.

The photograph on the second sheet is a close-up view of typical flowers of 'Koncasmile'.

DETAILED BOTANICAL DESCRIPTION

The aforementioned photographs and following observations and measurements describe plants of the new *Alstroemeria* grown during the summer and early autumn in 19-cm containers in a glass-covered greenhouse in Nieuwveen, The Netherlands and under cultural practices typical of commercial potted *Alstroemeria* production. During the production of the plants, day temperatures ranged from 6° C. to 35° C. and night temperatures ranged from 6° C. to 20° C. Plants were 36 weeks old when the photographs and description were taken. In the following description, color references are made to The Royal Horticultural Society Colour Chart, 2001 Edition, except where general terms of ordinary dictionary significance are used.

Botanical classification: *Alstroemeria hybrida* 'Koncasmile'.

Parentage:

*Female, or seed, parent*.—Proprietary *Alstroemeria hybrida* selection identified as code number 11-11-0-7, not patented.

*Male or pollen parent*.—Proprietary *Alstroemeria hybrida* selection identified as code number 12-lele, not patented.

Propagation:

*Type*.—In vitro rhizogenesis.

*Root description*.—Thick, fleshy; color, close to 159D.

*Rooting habit*.—Freely branching; dense.

*Rhizome description*.—Shape: Elongate; rounded. Length: About 3 cm to 7 cm. Diameter: About 1 cm. Texture: Smooth. Color: Close to 156D.

Plant description:

*Plant habit*.—Compact and mounded; freely branching habit, bushy appearance; sturdy and strong plants; vigorous growth habit.

*Plant height*.—About 30 cm.

*Plant diameter* (*area of spread*).—About 40 cm.

Stem description:

*Aspect*.—Mostly upright to somewhat outwardly spreading.

*Internode length*.—About 0.3 cm to 2.5 cm.

*Strength*.—Strong, sturdy.

*Texture*.—Ciliate.

*Color*.—Towards the base, close to 187B; mid-section, shifting to close to 148C; towards the apex, close to 147C.

Foliage description:

*Arrangement*.—Alternate; below the peduncle, arranged in a single whorl; leaves sessile.

*Length*.—About 3 cm to 13.5 cm.

*Width*.—About 1.4 cm to 3.4 cm.

*Shape*.—Lanceolate to oblong.

*Apex*.—Acute.

*Base*.—Attenuate.

*Margin*.—Entire.

*Texture, upper and lower surfaces*.—Smooth, glabrous; margin, ciliate.

*Venation pattern*.—Parallel.

*Color*.—Developing leaves, upper surface: Close to 137B. Developing leaves, lower surface: Close to 138A. Fully expanded leaves, upper surface: Close to 137A; venation, close to 137A. Fully expanded leaves, lower surface: Close to 137C; venation, close to 137C.

Flower description:

*Flower type and habit*.—Single cup-shaped flowers arranged in compound umbels; flowers face upright to outwardly; freely flowering habit; about two to ten flowers per inflorescence; and about 20 to 60 flowers developing per plant.

*Natural flowering season*.—Flowering continuous from the late spring until the autumn in The Netherlands.

*Fragrance*.—None detected.

*Flower longevity on the plant*.—About one to three weeks; flowers not persistent.

*Flower longevity as a cut flower*.—About one to two weeks; flowers not persistent.

*Flower buds*.—Length: About 4 cm. Diameter: About 1.6 cm. Shape: Ovoid. Color: Close to 145C; apex, close to 143A.

*Umbel height*.—About 12 cm.

*Umbel diameter*.—About 14 cm.

*Flower diameter*.—Large, about 9.5 cm.

*Flower depth* (*height*).—About 5.2 cm.

*Perianth*.—Arrangement: Six arranged in two whorls, each whorl with two lateral and one median segments. Size, inner perianth: Length, lateral segments: About 6.5 cm. Width, lateral segments: About 2.3 cm. Length, median segment: About 5.2 cm. Width, median segment: About 2.5 cm. Size, outer perianth: Length, lateral segments: About 6.7 cm. Width, lateral segments: About 3.8 cm. Length, median segment: About 6 cm. Width, median segment: About 3.9 cm. Shape, inner perianth, lateral and median segments: Oblanceolate. Shape, outer perianth, lateral and median segments: Obovate. Apex, inner perianth, lateral and median segments: Acute. Apex, outer perianth, lateral and median segments: Emarginate. Base, inner and outer perianths, lateral and median segments: Attenuate. Margin, inner and outer perianths, lateral and median segments: Serrate. Texture, inner and outer perianths, lateral and median segments: Smooth, glabrous. Color, inner perianth: When opening, lateral segments, upper surface: Towards the apex and base, close to 76D; mid-section, close to 1A; at the apex, close to 71B; stripes, close to 187A. When opening, median segment, upper surface: Towards the apex and base, close to 69D; mid-section, close to 2B; stripes, close to 187C. When opening, lateral segments, lower surface: Towards the apex and base, close to N155A; mid-section, close to 1B; stripes, close to 198A. When opening, median segment, lower surface: Towards the apex and base, close to N155B; mid-section, close to 2B; stripes, close to 198A and 185A. Fully opened, lateral segments, upper surface: Towards the apex and base, close to 76D; mid-section, close to 14B; stripes, close to 187B. Fully opened, median segment, upper surface: Towards the apex and base, close to 69D; mid-section, close to 13A; stripes, close to 187C. Fully opened, lateral segments, lower surface: Towards the apex and base, close to N155A; mid-section, close to 11A; stripes, close to 198A. Fully opened, median segment, lower surface: Towards the apex, close to N155A; mid-section, close to 11B; towards the base, close to N155B; stripes, close to 198A and 185A. Color, outer perianth: When opening, lateral segments, upper surface: Apex, close to N74A; towards the apex, close to N155A; mid-section, close to 155A, N74D and 2B; towards the base, close to 155B. When opening, median segment, upper surface: Apex, close to N74A; towards the apex, close to N155A; mid-section, close to N74D and 2B; towards the base, close to 155B. When opening, lateral and median segments, lower surface: Towards the apex, close to 45A and N155A; mid-section, close to 75A, N155A and 11B; towards the base, close to 75A and N155A. Fully opened, lateral segments, upper surface: Towards the apex, close to N155A; mid-section, close to 7A and 70B; towards the base, close to 76D. Fully opened, median segment, upper surface: Towards the apex, close to N155A; mid-section, close to 10C and 70B; towards the base, close to 76D. Fully opened, lateral and median segments, lower surface: Towards the apex, close to 45A and N155A; mid-section, close to 75A, N155A and 11B; towards the base, close to 75A and N155A.

*Pedicels*.—Length: About 1 cm to 3.5 cm. Diameter: About 2 mm to 6 mm. Strength: Strong. Angle: Erect to about 70° from vertical. Texture: Smooth, glabrous. Color: Close to 146A.

*Reproductive organs*.—Stamens: Quantity per flower: Six. Anther shape: Oval. Anther size: About 2 mm by 7 mm. Anther color: Close to 148B. Pollen amount: Abundant. Pollen color: Close to 189A. Pistils: Quantity per flower: One. Pistil length: About 4.7 cm. Style length: About 3.3 cm. Style color: Close to 75A. Stigma color: Close to 69D. Ovary color: Close to 146B.

*Fruits*.—Length: About 9 mm. Diameter: About 7 mm. Color: Close to 199A.

*Seeds*.—Seed production has not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate wind, rain and temperatures ranging from about 6° C. to about 35° C.

It is claimed:

1. A new and distinct *Alstroemeria* plant named 'Koncasmile' as illustrated and described.

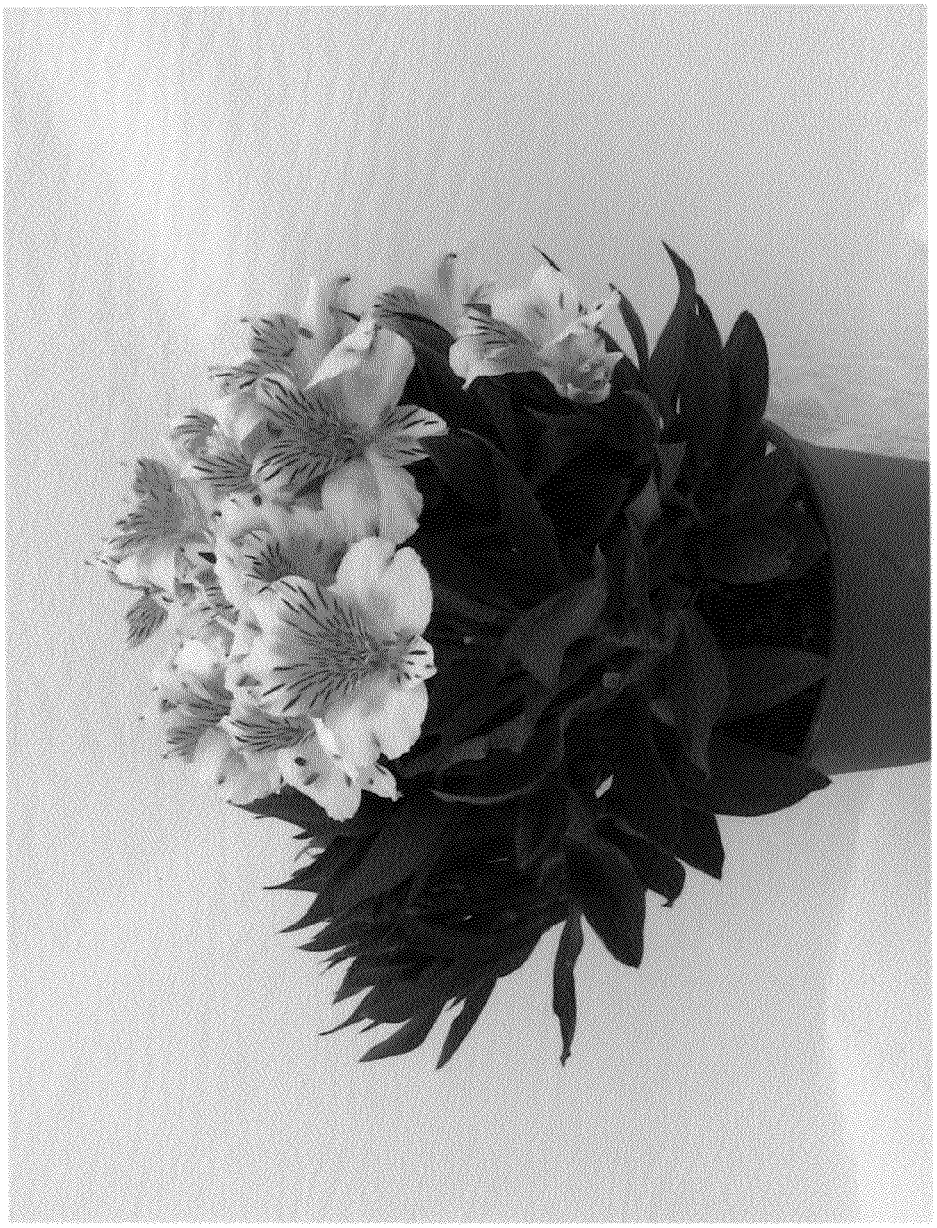

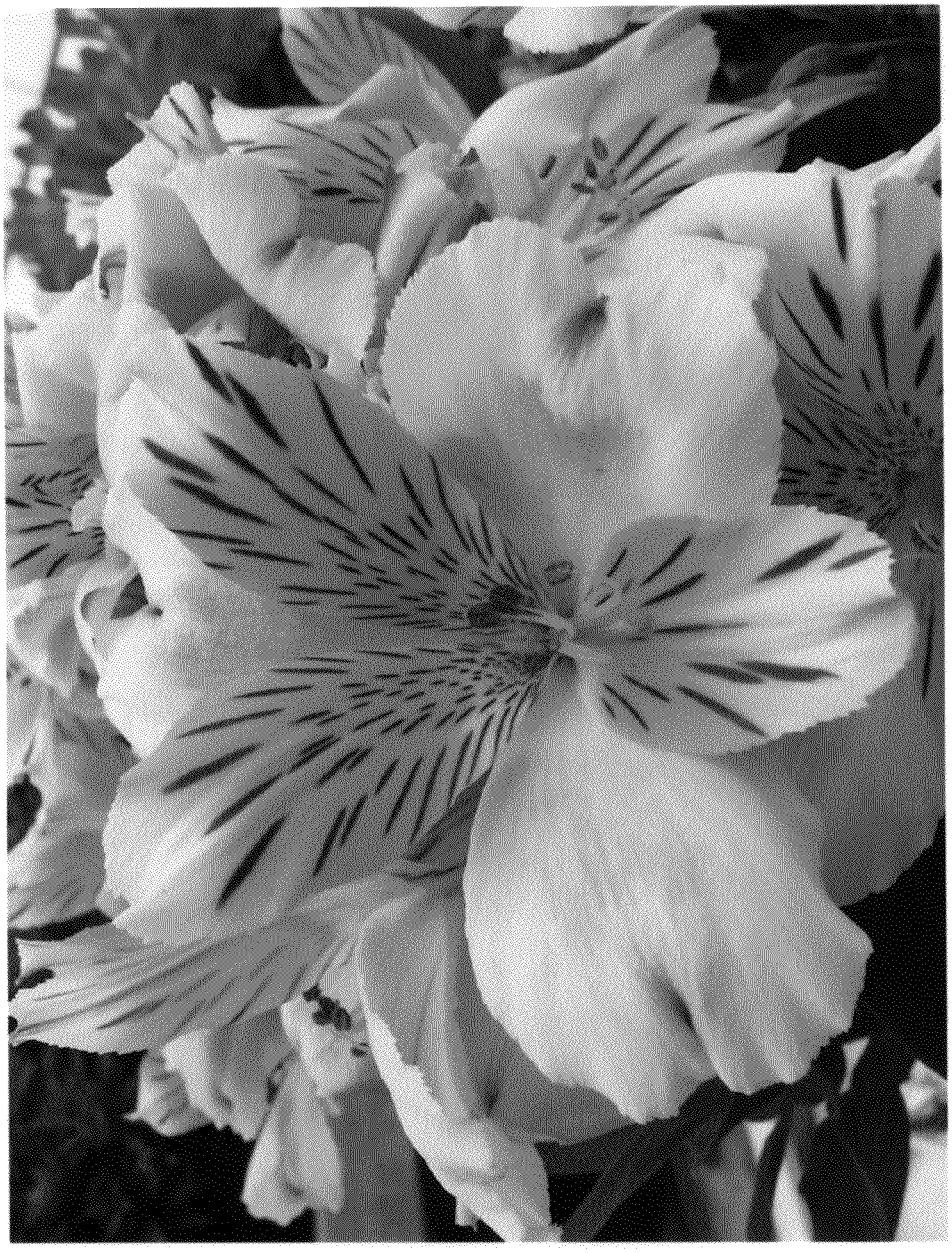

* * * * *